United States Patent
Schweikard et al.

(10) Patent No.: US 7,167,738 B2
(45) Date of Patent: Jan. 23, 2007

(54) METHOD FOR NAVIGATING IN THE INTERIOR OF THE BODY USING THREE-DIMENSIONALLY VISUALIZED STRUCTURES

(75) Inventors: Achim Schweikard, Hamburg (DE); Manfred Doetter, Munich (DE); Michael Roth, Augsburg (DE); José-Luis Moctezuma de la Barrera, Freiburg (DE)

(73) Assignee: Stryker Leibinger GmbH & Co., KG, Freiburg (DE)

( * ) Notice: Subject to any disclaimer, the term of this patent is extended or adjusted under 35 U.S.C. 154(b) by 830 days.

(21) Appl. No.: 10/089,357

(22) PCT Filed: Jul. 31, 2001

(86) PCT No.: PCT/EP01/08844

§ 371 (c)(1),
(2), (4) Date: Sep. 24, 2002

(87) PCT Pub. No.: WO02/09611

PCT Pub. Date: Feb. 7, 2002

(65) Prior Publication Data

US 2004/0082849 A1    Apr. 29, 2004

(30) Foreign Application Priority Data

Aug. 1, 2000    (DE) ................ 100 37 491

(51) Int. Cl.
*A61B 5/05*    (2006.01)
*G06K 9/00*    (2006.01)

(52) U.S. Cl. .............. 600/407; 600/411; 600/425; 382/131; 382/174

(58) Field of Classification Search .......... 600/407, 600/410–411, 425, 427; 378/4, 11, 21; 382/131, 382/174
See application file for complete search history.

(56) References Cited

U.S. PATENT DOCUMENTS

| | | | | |
|---|---|---|---|---|
| 4,305,127 A | * | 12/1981 | Heuscher | 600/425 |
| 4,899,318 A | | 2/1990 | Schlumberger et al. | 367/8 |
| 5,274,551 A | * | 12/1993 | Corby, Jr. | 600/433 |
| 5,375,156 A | * | 12/1994 | Kuo-Petravic et al. | 378/9 |
| 5,475,422 A | * | 12/1995 | Mori et al. | 348/48 |
| 5,532,595 A | * | 7/1996 | Lampman et al. | 324/309 |
| 5,625,660 A | * | 4/1997 | Tuy | 378/15 |
| 5,852,646 A | | 12/1998 | Klotz et al. | |
| 6,061,469 A | * | 5/2000 | Walterman | 382/154 |
| 6,542,573 B1 | * | 4/2003 | Schomberg | 378/19 |
| 6,618,468 B1 | * | 9/2003 | Klotz et al. | 378/98.12 |
| 6,944,359 B1 | * | 9/2005 | Kamei et al. | 385/12 |

FOREIGN PATENT DOCUMENTS

| | | |
|---|---|---|
| DE | 39 15 370 | 11/1989 |
| DE | 196 20 371 | 12/1997 |
| DE | 197 46 092 | 5/1999 |
| DE | 198 07 884 | 9/1999 |
| WO | WO 91/07726 | 5/1991 |

OTHER PUBLICATIONS

Declaration of Non-Establishment of International Search Report (Jan. 2, 2002), Appl. No. PCT/EP01/08844.
Morneburg, H., "Bildgebende Systeme fur die medizinische Diagnostik", *Publics MCD Verlad*, 1995 (110-116) (with translation of Sect. 5.1.4).
Nassi et al., "Iterative Reconstruction-Reprojection: An Algorithm for Limited Data Cardiac-Computed Tomography".

* cited by examiner

*Primary Examiner*—Francis J. Jaworski
(74) *Attorney, Agent, or Firm*—McCracken & Frank LLP

(57) ABSTRACT

A method is described for navigating in the interior of the body using three-dimensionally visualized structures. In a first step of the method, at least two two-dimensional images of the same anatomical object are provided from different perspectives, and also items of information that make it possible to draw conclusions about the respective spatial position of an imaging system relative to the anatomical object. The projections of a geometrical structure to be visualized are then created in every two-dimensional image, wherein a geometrical structure to be visualized is created in each two-dimensional image, wherein the geometrical structure to be visualized is different from the anatomical object. A cone surface is then generated in space for each image wherein the spatial positions of the cone vertex and cone directrix are determined from the respective spatial position of the imaging system and the shape of the cone directrix is determined from the shape of the projection of the geometrical structure to be visualized on the image. Finally, a spatial intersection of the individual cone surfaces is formed to determine the geometrical structure and the geometrical structure determined and/or an intersection of a plurality of geometrical structures determined are/is represented and the representation is used for navigation.

13 Claims, 8 Drawing Sheets

METHOD FOR NAVIGATING IN THE INTERIOR OF THE BODY USING THREE-DIMENSIONALLY VISUALIZED STRUCTURES

This application is a 371 pf PCT/EP01/08844 filed Jul. 31, 2001.

BACKGROUND OF THE INVENTION

The invention relates to a method for navigating, for example a surgical instrument or an endoscope, in the interior of the body using three-dimensionally visualized structures.

During surgical operations, an attempt is made, as a rule, to make as small a cut as possible through the skin of the patient. Said cut is often just big enough in order to be able to reach the anatomical structure to be treated in the interior of the body with surgical instruments. For this reason, it is difficult for the surgeon and often even impossible to survey optically those anatomical structures of the patient that are relevant to the operation. Even the position, for example, of surgical instruments relative to an anatomical object to be treated is often not visible to the surgeon. For this reason, methods of visualizing structures in the interior of the body for the purpose of navigating such instruments are increasingly gaining in importance.

DE 198 07 884 A1 describes a method for navigating a surgical instrument in the interior of the body. In accordance with this method, a plurality of images are made from various positions and orientations by means of an imaging device and the relative positions and orientations of the images with respect to one another are determined. Then, with the aid of said images, the relative position of an anatomical target object with respect to the surgical instrument is intraoperatively determined and visualized. Both for the precise planning of an operation and for the optical monitoring of the course of the operation, two-dimensional images, such as X-ray images, are as a rule inadequate. There is therefore a requirement to use three-dimensional representations.

Such three-dimensional representations can be generated, for example, by means of computer tomography (CT). Because of the equipment factors and because of the high computational expenditure, CT methods are primarily used to obtain preoperative data. CT methods are therefore unsuitable for an intraoperative visualization, i.e. a visualization taking place during the operation. Furthermore, the high radiation exposure accompanying the CT methods is in many cases undesirable for the patient.

To avoid high radiation exposure, thought can be given to generating the three-dimensional representations needed to plan the operation and to monitor the course of the operation from two or more two-dimensional representations. Such a method is described, for example, in U.S. Pat. No. 4,899,318.

SUMMARY OF THE INVENTION

The object of the invention is to provide a method for navigating using three-dimensionally visualized structures in the interior of the body, which method avoids high exposures of the patient to radiation, is associated with low computational expenditure and is therefore suitable, in particular, also for intraoperative use.

According to the invention, this object is achieved in that, in a first step, at least two two-dimensional images of the same anatomical object from different perspectives and also of information about the respective spatial position of the imaging system relative to the anatomical object are provided. In a second step, a projection of at least one geometrical structure to be visualized is then defined in each of the two-dimensional images, wherein the geometrical structure to be visualized is different from the anatomical object. In a third step, a conical surface is generated in space for each of the images, wherein the spatial positions of cone vertex and cone directrix are determined from the spatial position of the imaging system and the shape of the cone directrix is determined from the projection determined for the geometrical structure to be visualized on the respective image. In a fourth step, the spatial intersection of the individual conical surfaces is formed, wherein said spatial intersection corresponds to the geometrical structure to be visualized in the interior of the body. Then the geometrical structure determined in this way or an intersection of a plurality of geometrical structures determined in this way or both the structures and their intersection are represented graphically and the representation is used for navigation.

Expediently, either the anatomical object or, for example, a surgical instrument, or both, are also graphically represented three-dimensionally as navigation aid in addition to the geometrical navigation structure. The three-dimensional representation of the anatomical object and of the surgical instrument may, in this connection, be obtained in the same way as or in a similar way to the three-dimensional representation of the geometrical structure.

In accordance with the present invention, a three-dimensional model of the geometrical structure to be visualized is consequently prepared from projections created on the basis of a few two-dimensional images and this model is used for navigation. Since, in the simplest case, only two two-dimensional images have to be present and these two images do not necessarily have to be prepared by an image-forming method that uses X-ray radiation or another high-energy radiation, the radiation exposure for the patient is negligibly small in the visualization method according to the invention compared with conventional CT methods. Since, in addition, the amounts of data to be processed are also relatively small, in particular, compared with CT methods, the visualization can be performed extremely rapidly and even intraoperatively in order to provide the surgeon with actual information about the course of the operation. Furthermore, the exposure to radiation can be appreciably reduced for the OP team.

The projections can be created on the basis of the images in various ways, for example automatically, partially automatically or manually. Expediently, the creation takes place in such a way that, after the creation, information relating to the created projections is available in the form of digital data and can be further processed for the purpose of visualization in a computer-aided manner.

The shape of the geometrical structure to be visualized is simultaneously determined during the creation of the projection of the geometrical structure on the basis of individual images. The projection to be created in a certain image may, for example, be a point, a straight line, a circular segment or any other structure having the form of a line. The geometrical structure to be visualized may be any one-dimensional, two-dimensional or three-dimensional structure, such as a point, a straight line, a plane or a cone.

The geometrical structure to be visualized does not correspond to the anatomical object imaged on the basis of the two-dimensional image, but may be derived from it. Thus, for example, a circular-segment projection may be created in the region of the ball-shaped head of the femur bone on the basis of an image of a femur bone in order to visualize a navigation aid in the shape of a geometrical sphere structure. Navigation using geometrical structures visualized in this way has the advantage over navigation using, for example, the femur bone or a model of the femur bone in that it is simpler, clearer and, therefore, also safer and more rapid. The operation time can therefore not only be shortened by means of the navigation method according to the invention, but also the operation safety can be increased.

The determination of items of information that permit conclusions to be drawn about the spatial positions of the imaging system in which the image has been recorded may take place in a variety of ways. Thus, for example, the spatial position of the imaging system may be unalterable and, as a rule, known in advance, and the position of the anatomical object may be changed from image to image. The associated imaginary perspective can then be calculated back from the respective position of the anatomical object assuming a positionally fixed anatomical object.

On the other hand, it is also possible, and often even expedient, to place the anatomical object in space in a positionally fixed manner and to alter the spatial position of the imaging system from image to image. To determine the respective spatial positions of the imaging system, a tracking system known from the prior art is preferably used in this case. If an X-ray imaging system having a C-shaped support arm is used, a marker may be applied to the C-shaped support arm for an infrared tracking system installed in space. The precise spatial position of the C-shaped support arm, which permits a conclusion to be drawn about the spatial position of an X-ray source and an X-ray detector, can then be determined by means of the tracking system. The spatial position of the X-ray source and of the X-ray detector determines the spatial position of the conical surface. Furthermore, the position of the C-shaped support arm can be determined by using a positionally fixed robot. The robot moves a calibration object provided with marks impervious to X-rays in the beam path of the C-shaped support arm. From the position of the marks in the image, the position of the C-shaped support arm can be calculated.

The individual two-dimensional images can be prepared in various ways. Depending on the imaging method, the spatial positions of the cone vertex and cone directrix are determined in various ways. In the X-ray imaging method already mentioned and preferably used, the anatomical object and, if applicable, also the surgical instrument are disposed between an X-ray source and an X-ray detector. In the simplest case, the spatial position of the X-ray source corresponds to the spatial position of the cone vertex and the spatial position of the X-ray detector to the spatial position of the cone directrix. If X-ray optics are used, the spatial positions of the cone vertex and cone directrix can be calculated back from the characteristic data of the X-ray optics. Even if the two-dimensional images have been prepared by image-forming methods other than X-ray methods (infrared methods, ultrasonic methods, MR methods, etc.), it is necessary, as a rule, to take account of the respective system parameters of the imaging system in addition in the determination of the spatial position of the cone vertex and cone directrix.

Advantageously, a conical surface is generated in space for every two-dimensional image. A conical surface is produced by moving a straight line that passes through a fixed point, the cone vertex, along a curve, the cone directrix. The cone directrix consequently determines the shape of the conical surface.

The cone directrix may be a straight line that is created, for example, as the preferred direction desired by the surgeon in the individual images. The preferred direction may characterize that direction from which, for example, an endoscope or a surgical instrument is to approach an anatomical object to be treated. If the cone directrix is a straight line, the associated conical surface has a triangular shape.

In the extreme case, the cone directrix may also be a point that is created, for example, as target position in each of the images. Said target position may characterize a place at which a surgical intervention is to take place. In the case of a punctiform cone directrix, the associated conical surface has the shape of a straight line.

In contrast to the three-dimensional visualization of an anatomical object, such as a femur bone, which can take place only approximately using only two images (see FIG. 4), a preferred direction to be visualized or a sphere to be visualized can be created precisely and unambiguously by means of two images, i.e. by means of the intersection of two cones.

In accordance with a preferred embodiment of the invention that may be used regardless of the visualization of the geometrical structure, at least one further data set that has been prepared preoperatively or intraoperatively can be used for the refining correction of, for example, an approximation model of an anatomical object after the formation of the spatial intersection of individual conical surfaces. Said further data set may be a data set prepared by a magnetoresonance method (MR method). MR tomography has the advantage that it is not associated with any exposure of the patient to radiation. It may, for example, refine a three-dimensional representation of an anatomical object generated from two-dimensional X-ray images by means of one or more MR images. Conversely, it is possible, with the aid of additionally recorded X-ray images, to refine a three-dimensional representation of the anatomical object generated from two-dimensional MR images.

Thus, for example, thought may be given to providing at least two two-dimensional X-ray images of the same bone from different perspectives that permit conclusions to be drawn about the respective spatial position of the X-ray imaging system relative to the bone and also an MR data set of the bone. A projection can then be created of a surface or of an outline of the spongiosa of the bone in every two-dimensional X-ray image and a conical surface in space can be generated for every X-ray image, the spatial position of cone vertex and cone directrix being determined from the respective spatial position of the imaging system and the shape of the cone directrix can be determined from the shape of the projection. To determine a first model of the surface of the spongiosa, a spatial intersection can be formed of the individual conical surfaces and a second model of the spongiosa can be determined from the MR data set. A representation of the bone can then be generated by combining the two models, it being possible, for example, to navigate using the representation. The first three-dimensional model can also be determined in another way as explained above.

The geometrical structure resulting from the spatial intersection of the conical surfaces or an approximation model of the anatomical object may be corrected by a data set which is such that it contains a generic, shape-variable model of the structure or of the object. Such a generic model can be derived, for example, from anatomical atlases or from an exact model of a patient comparable according to age, sex, origin etc.

In accordance with a further aspect of the invention, after the calculation of a three-dimensional representation, for example, of a geometrical structure, of an anatomical object or of a surgical instrument, an inverse calculation may be made in order to determine suitable spatial positions of the imaging system for further two-dimensional images in order to improve the representation. Preferably, these calculations may be performed intraoperatively and still processed appropriately during the operation in order gradually to refine the initial representation. Thus, imaging directions may be indicated to the surgeon for the C-shaped support arm of an X-ray imaging system from which a fluoroscopy appears expedient on the basis of previous calculations.

In the case of intraoperative visualization, the actual position of an instrument to be navigated, such as a surgical instrument, an endoscope, etc., is preferably represented simultaneously in addition to the anatomical structure to be treated. The position of the instrument relative to the anatomical structure to be treated can be determined in various ways. Thus, for example, the marker of a tracking system may be applied to the instrument and the actual position of the instrument determined with the aid of the tracking system. On the other hand, it would also be conceivable to determine the position of the instrument with the aid of the visualization method according to the invention. Preferably, in addition to the instrument, the effective axis of the instrument is also represented. The effective axis indicates for example, that direction in which a surgical instrument is applied.

Furthermore, the actual spacing of the instrument from the anatomical object to be treated can also be indicated.

In addition to the geometrical structure to be visualized, the individual two-dimensional images that underlie the visualization of the geometrical structure can also be represented graphically at the same time. The individual two-dimensional images can be arranged in the representation in such a way that their spatial position in the graphical representation corresponds to their respective perspective.

In accordance with a further embodiment of the invention, a navigation aid may be formed for the instrument in the above-described graphical representation of the geometrical structure to be visualized or in a separate representation. The navigation aid indicates for example, the actual position of the effective axis of the surgical instrument relative to a preferred direction to be visualized in the form of a tunnel structure. The navigation aid may comprise, furthermore, directional arrows that facilitate the alignment of the effective axis along the preferred direction.

BRIEF DESCRIPTION OF THE DRAWINGS

Further advantages and details of the invention emerge from the exemplary embodiments and the figures. In the figures.

DESCRIPTION OF THE PREFERRED EMBODIMENT

Figure 1:
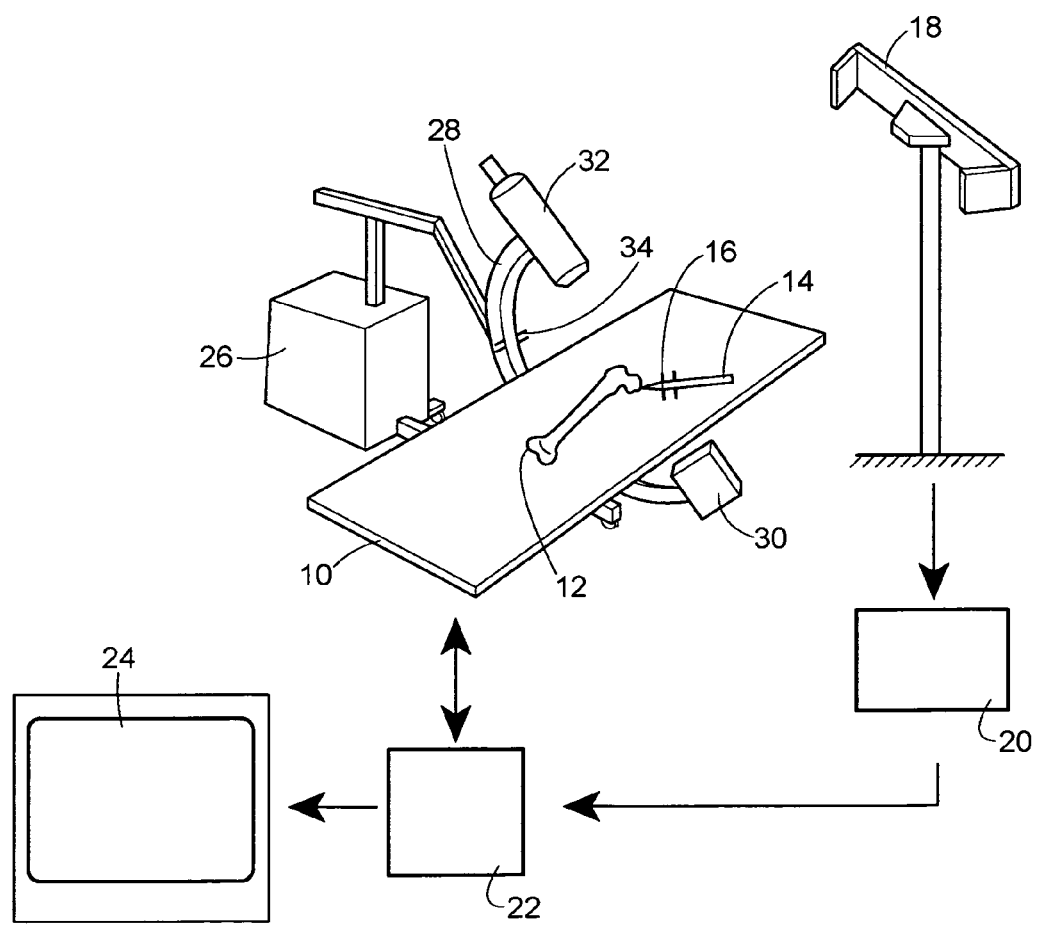
FIG. 1 shows a diagrammatic representation of a surgical intervention with the aid of a tracking system.

FIG. 1 shows diagrammatically an operation scenario based on the visualization method according to the invention. Disposed on an operating table 10 is an anatomical object to be treated operatively in the form of a femur bone 12. The surgical intervention is performed with the aid of a surgical instrument 14. Attached to the surgical instrument 14 is a marker 16 of an infrared tracking system. Said marker 16 is designed to transmit infrared radiation. The infrared tracking system comprises, furthermore, an infrared detector 18 disposed in a positionally fixed manner. A localization computer 20 of the tracking system calculates the actual spatial position of the surgical instrument 14 provided with the marker 16 from the signals received by the infrared detector 18. The calculated spatial co-ordinates are transmitted by the localization computer 20 via a data bus to a central computer 22, where they are processed graphically and represented graphically on a viewing screen 24.

FIG. 1 shows, furthermore, an X-ray imaging system 26 having a C-shaped support arm 28. Disposed at one of the two ends of the C-shaped support arm 28 is an X-ray source 30 and at the opposite end of the C-shaped arm 28 an X-ray detector 32. The two-dimensional images prepared by the X-ray imaging system 26 are fed via a data bus to the central computer 22 in digitized form. At the same time, the central computer 22 also serves to control the X-ray imaging system 26.

A plurality of two-dimensional images has already been prepared in the run-up to the surgical intervention by the X-ray imaging system 26 and processed according to the invention in the central computer 22. In the X-ray imaging system 26, the spatial position of the perspective is determined by the spatial position of the X-ray source 30 and the spatial position of the image plane is determined by the spatial position of the X-ray detector 32. To determine the spatial position of X-ray source 30 and X-ray detector 32, a further marker 34, whose structure corresponds to the structure of the marker 16 disposed on the surgical instrument 14, is attached to the C-shaped support arm 28 of the X-ray imaging system 26. Consequently, in addition to the spatial position of the surgical instrument 14, the spatial position of the perspective and the image plane can also be determined by means of the infrared detector 18 of the infrared tracking system. The relevant items of information are likewise made available to the central computer 22 via the localization computer 20.

The central computer 22 generates a three-dimensional approximation model of the femur bone 12 from the intraoperatively obtained two-dimensional images and represents said approximation model, a geometrical structure to be visualized and also the relative position of the surgical instrument 14 with respect to the femur bone 12 or to the geometrical structure, graphically on the viewing screen 24.

The performance of the visualization method according to the invention is explained in greater detail below with reference to FIGS. 2 to 12.

Figure 2:
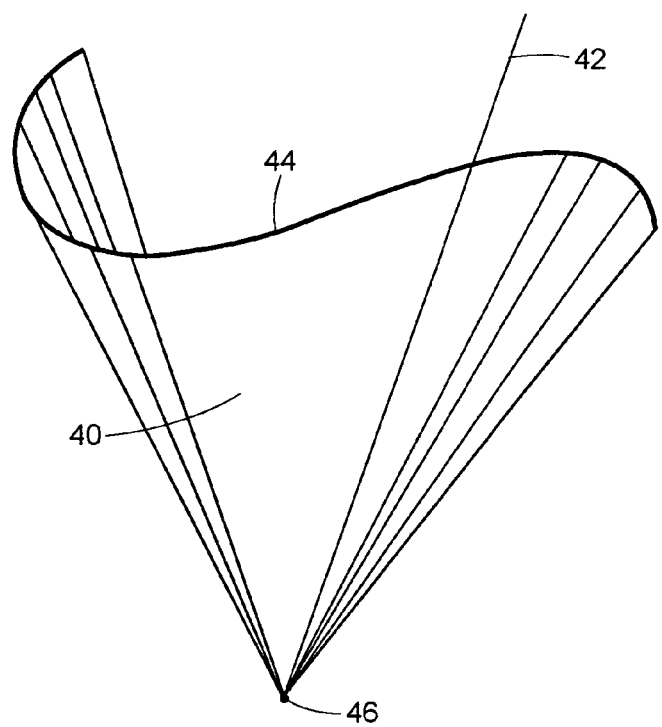
FIG. 2 shows a diagrammatic representation of a conical surface.

FIG. 2 shows a conical surface 40. Said conical surface 40 is produced by moving a straight line 42, which passes through the cone vertex 46, along the cone directrix 44. Proceeding from the vertex 46 of the cone, the conical surface extends along the straight line 42 to infinity and includes the directrix 44.

Figure 3:
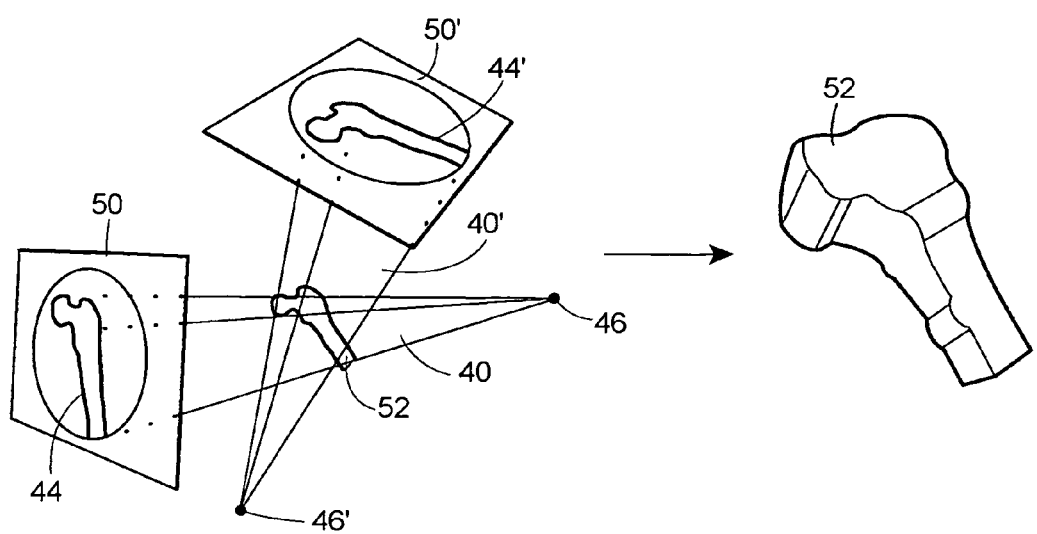
FIG. 3 shows the determination of a model of a structure to be visualized with the aid of the spatial intersection of two conical surfaces.

After the generation of a conical surface has been explained by way of example in FIG. 2, the three-dimensional visualization by means of conical surfaces is revealed by considering FIG. 3. FIG. 3 shows two conical surfaces 40 and 40' in their relative spatial arrangement with respect to one another. Furthermore, FIG. 3 shows two two-dimensional images 50, 50' that were recorded by the X-ray imaging system 26 shown in FIG. 1. The spatial positions of the cone vertices 46, 46' of the two cones 40, 40' are created by the spatial positions of the X-ray source with respect to the recording time of the two images 50, 50'. The shape of each cone directrix 44, 44' is determined by the particular outline of the femur bone shown by way of example in the images 50, 50'. In FIG. 3, the two images 50, 50' are disposed in that spatial position in which the respective image planes were situated.

An approximation model 52 of the anatomical object in the form of the femur bone 12 shown in the original in FIG. 1 is obtained by forming the spatial intersection of the conical surface 40 with the conical surface 40'.

As can be inferred from FIG. 3, the approximation model 52 of the femur bone is still comparatively coarse. The model 52 can be refined in that, in addition to the two images 50, 50', yet further images of the femur bone 12 are recorded from additional perspectives and the approximation model is then determined on the basis of the spatial intersection of three or more conical surfaces.

A further possibility for improving the approximation model 52 is to take account of a preoperatively determined MR data set of the femur bone shown in FIG. 1 in preparing the approximation model 52. Specifically, a three-dimensional model of the femur bone 12 can also be calculated with the aid of MR tomography.

A typical bone is made up of a soft core tissue (spongiosa) that is enclosed by a thin layer of hard tissue (corticalis). The thickness of the corticalis layer is variable. Although the use of MR tomography is desirable, the corticalis layer is very difficult to segment automatically in MR images. However, both the edge of the corticalis layer and the underlying edge of the spongiosa are visible in the X-ray image. A basic problem in MR tomography is therefore that only the spongiosa of the femur bone is imaged with good visibility, whereas the outer corticalis layer appears black. The three-dimensional model obtained from the MR data set does not consequently correspond to the actual shape of the femur bone 12 since the outer corticalis layer is missing. Nevertheless, the MR model makes it possible to draw conclusions about the shape of the femur bone that can be used to refine the approximation model 52 shown in FIG. 3.

It is therefore possible to proceed as follows: the edge of the spongiosa is marked in the X-ray image and the surface of the spongiosa is automatically segmented in the nuclear spin image. A method for overlapping the last two structures (2D X-ray contours and 3D nuclear spin surface, each in the case of the spongiosa) can then be used for the registration step (spatial alignment of the position of the nuclear spin image with the X-ray images). Thus, the actual bone surface (with corticalis layer) can be visualized and function as a basis for navigation.

Thought can also be given to marking the contour of the spongiosa in the images 50, 50' shown in FIG. 3 and visualizing the spongiosa structure by the method according to the invention. In this way, the precise spatial position of the spongiosa structure can be determined. The shape of the spongiosa structure can then be revised using the MR data set.

Figure 4:
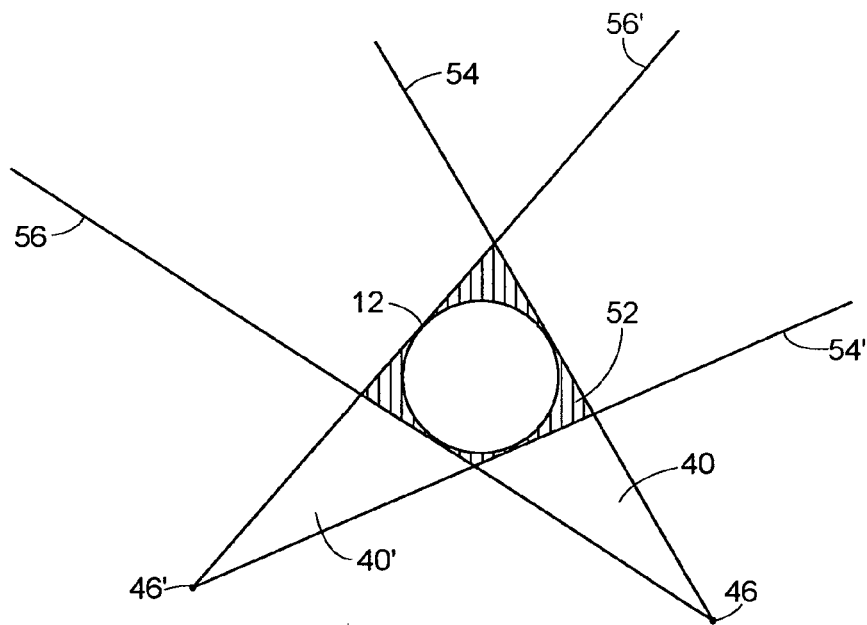
FIG. 4 shows the navigation of a surgical instrument with the aid of the two-dimensional images and of the model of the structure to be visualized.

FIG. 4 illustrates a two-dimensional section through the spatial arrangement shown in FIG. 3. The intersection plane shown in FIG. 4 contains the two cone vertices 46, 46' and also two straight lines 54, 56 that form the boundary of the conical surface 40 and two straight lines 54', 56' that form the boundary of the conical surface 40'. The region of the intersection of these four boundary straight lines 54, 56, 54', 56' establishes that cross section of the approximation model 52 that extends through the plane shown in FIG. 4.

FIG. 4 likewise shows the actual circular cross section of the femur bone 12. Consequently, the deviation of the cross section of the approximation model 52 from the actual cross section of the femur bone 12 can be inferred from FIG. 4. As is evident from FIG. 4, the deviation of the approximation model 52 from the actual shape of the femur bone 12 is particularly severe at those points where the boundary straight lines 54, 56, 54', 56' intercept. This insight can be used to optimize the perspectives in regard to the position of the planned surgical intervention.

Figure 5:
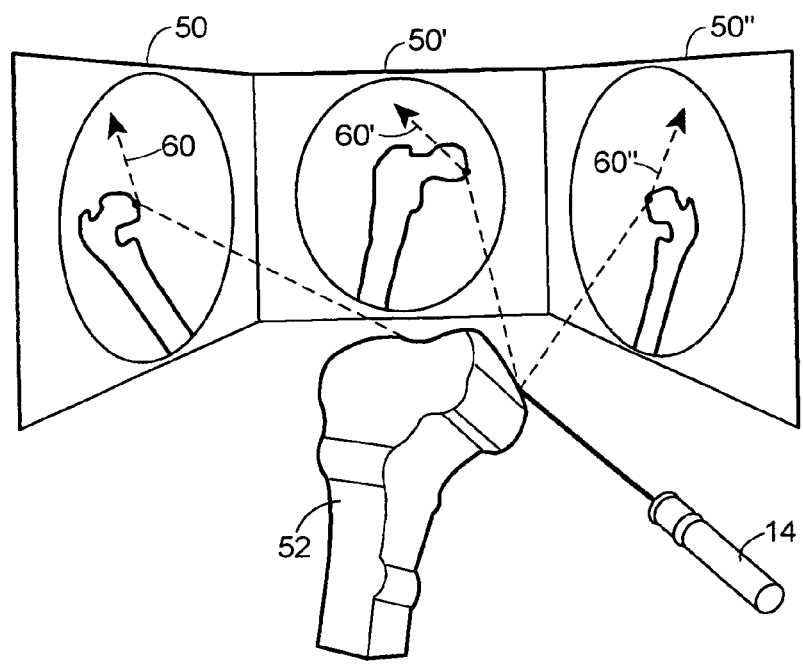
FIG. 5 shows a two-dimensional sectional view of the spatial intersection of two conical surfaces.

FIG. 5 shows diagrammatically a possible way of graphically representing intraoperatively the approximation model 52 determined by the above-described visualization method on the viewing screen 24 shown in FIG. 1. In addition to the approximation model 52, the actual position of the surgical instrument 14 relative to the approximation model 52 is also represented graphically. The actual position of the surgical instrument 14 is determined, as explained above, with the aid of the infrared tracking system shown in FIG. 1. To visualize the shape of the surgical instrument 14, recourse is made to a previously stored CAD data set.

In addition to the approximation model 52 and the surgical instrument 14, three two-dimensional images 50, 50', 50" of the femur bone 12 are also shown on the viewing screen 24. Said images 50, 50', 50" have been prepared with the aid of the X-ray imaging system 26 shown in FIG. 1. They are shown on the viewing screen 24 in regard to the approximation model 52 in that spatial position in which the X-ray detector 32 was situated relative to the femur bone 12 during production of the respective image 50, 50', 50". This facilitates the navigation of the surgical instrument 14 for the surgeon. The images 50, 50', 50" show, furthermore, the respective projections 60, 60', 60" of the effective axis of the surgical instrument 14.

Figure 6:
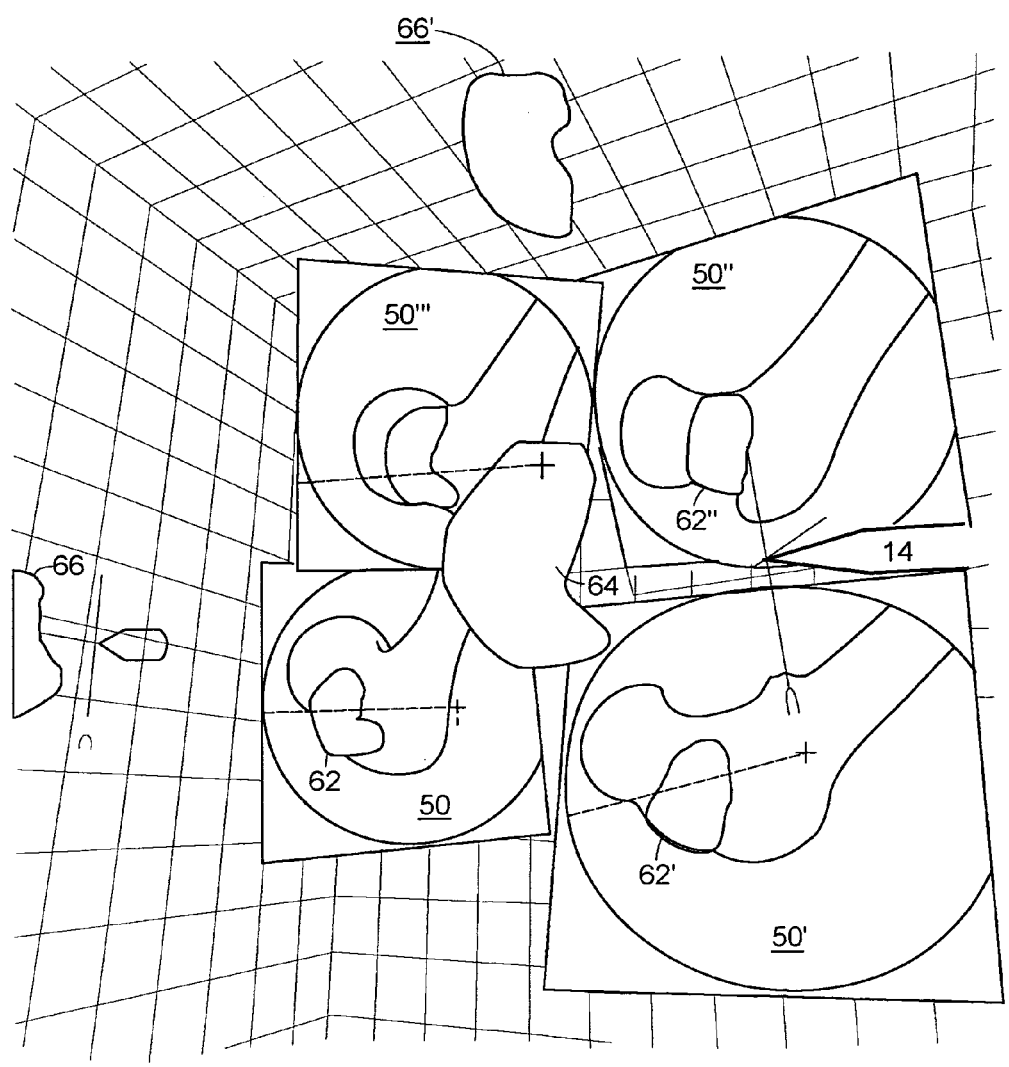
FIG. 6 shows a representation according to the invention of a surgical intervention on a viewing screen.

FIG. 6 shows a further possible way of intraoperatively representing the course of an operation graphically in the form of a viewing-screen printout. The representation in accordance with FIG. 6 substantially corresponds to the representation in accordance with FIG. 5. As a departure from FIG. 5, however, FIG. 6 does not show a three-dimensional approximation model of the entire femur bone, but only a three-dimensional approximation model 64 of a tumour that has attacked the femur bone. The three-dimensional approximation model 64 of the tumour is based on four two-dimensional images 50, 50', 50", 50''' of the femur bone. The four images 50, 50', 50", 50''' are graphically disposed in such a way that they reproduce that respective position of the X-ray detector 32 relative to the femur bone 12 in accordance with FIG. 1 in which the respective image 50, 50', 50", 50'" was prepared.

Each of the four images 50, 50', 50", 50'" contains a graphical representation 62, 62', 62", 62'" of the tumour. On the basis of the outlines of the four representations 62, 62', 62", 62'", four conical surfaces whose spatial intersection corresponds to the three-dimensional approximation model 64 of the tumour were generated, as explained with reference to FIG. 3.

The viewing-screen representation in accordance with FIG. 6 shows, furthermore, two projections 66, 66' of the approximation model 64 that additionally facilitate the monitoring of the surgical intervention for the surgeon. Furthermore, the spatial position of the surgical instrument 14 relative to the approximation model 64 is sketched in FIG. 6. The corresponding projection of the effective axis 60, 60', 60", 60'" of the surgical instrument 14 is sketched in each of the four images 50, 50', 50", 50'". This graphical measure also helps the surgeon to monitor the surgical intervention intraoperatively.

Figure 7:
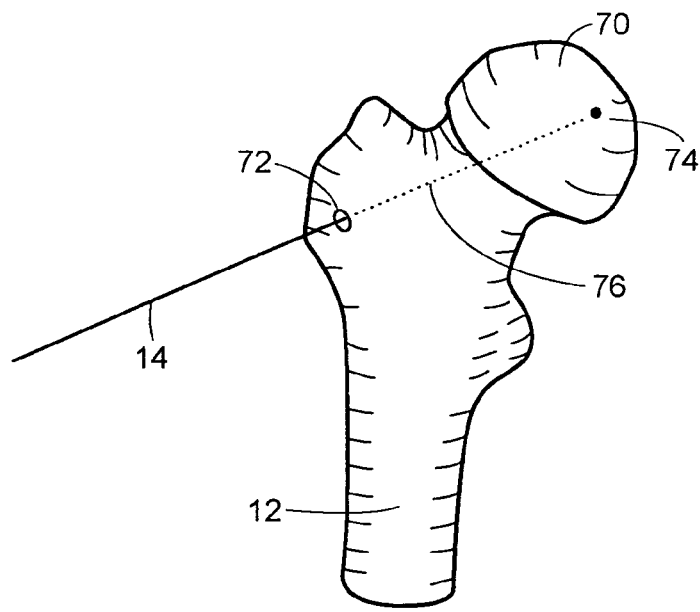
FIG. 7 shows a planned surgical intervention using a surgical drill.

Whereas the removal of a tumour is sketched in FIG. 6, the surgical intervention of a drilling in the ball-shaped head 70 of the femur bone 12 using a geometrical navigation structure is described below with reference to FIG. 7. In such a drilling, the problem is that the surgical instrument, namely the drill 14 illustrated in FIG. 7 is to be introduced into the femur bone 12 only down to a certain penetration depth since the drill 14 must not puncture a cartilage layer on the surface of the ball-shaped head 70 of the femur bone 12. The drill 14, which is to be introduced into the femur bone 12 in the position 72, must consequently not penetrate the femur bone 12 to such an extent that it reaches the puncture point 74.

Figure 8:
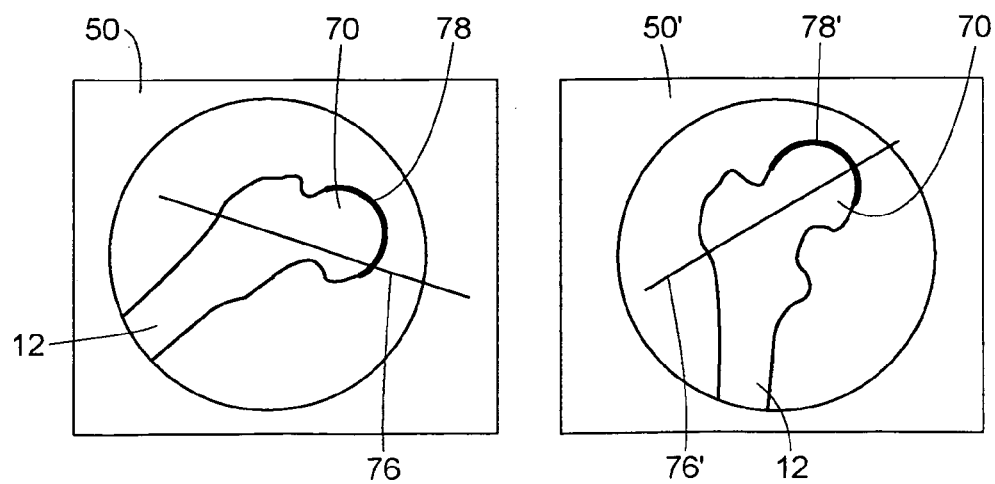
FIG. 8 shows two X-ray images for preparing the surgical intervention in accordance with FIG. 7.

Although the cartilage layer is visible on the ball-shaped head 70 of the femur bone 12 in X-ray images 50, 50' in accordance with FIG. 8, it is not possible to decide solely from individual two-dimensional X-ray images whether a drill has already punctured the cartilage layer. The reason for this is that an X-ray image provides only a projection of the head 70 of the femur bone 12 that, in general, makes the circular edge of the head 70 appear larger than it actually is.

The method according to the invention now makes possible, even if only two-dimensional X-ray images 50, 50' of the femur bone 12 are available, a safe navigation of the drill 14 in such a way that the head 70, 70' of the femur bone 12 is not punctured. Using the two images 50, 50' shown in FIG. 8, a preferred direction 76, 76' in which the drill 14 is to penetrate the head 70 of the femur bone 12 is, on the one hand, first characterized in each of them. On the other hand, the semicircular outline 78, 78' of the head 70, 70', respectively, is marked manually or by means of software for the purpose of contour extraction. In this way, the projections of the geometrical structures to be visualized are created.

Figure 9:
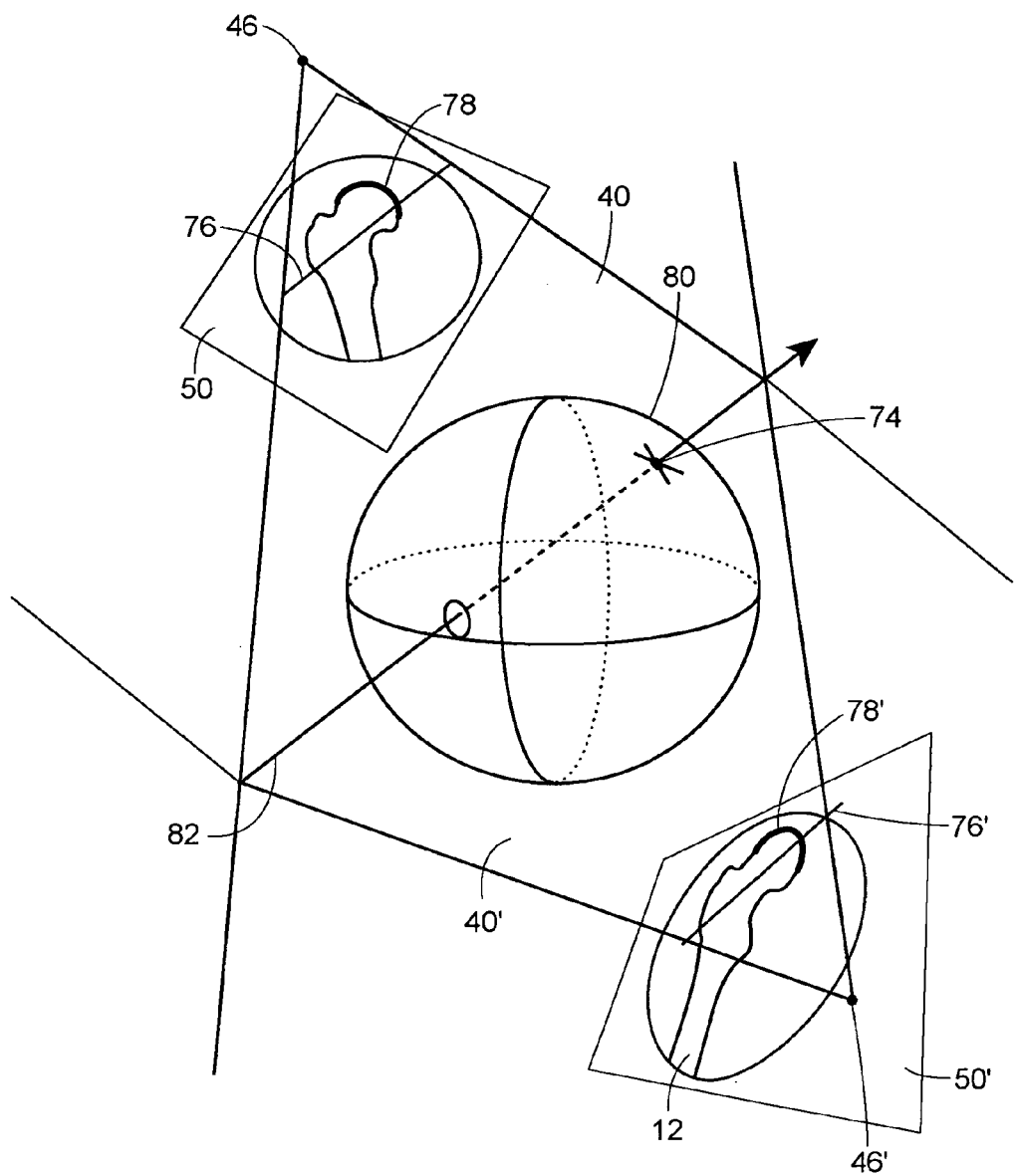
FIG. 9 shows the determination of a model of the structure to be visualized in accordance with FIG. 7.

FIG. 9 shows how the preferred direction 76, 76' and also a sphere corresponding to the surface of the head 70 of the femur bone 12 can be visualized three-dimensionally according to the invention using the two images 50, 50'. This visualization proceeds correspondingly as described above with reference to FIGS. 3 and 4.

Next, a spatial straight line 82 that corresponds to said preferred direction is determined from the two images 50, 50' using the respective preferred direction 76, 76' drawn in. Since the preferred direction 76, 76' marked in the two images 50, 50' is in each case part of a straight line, the two corresponding conical surfaces 40, 40' are present in the form of a flat triangle. As is evident from FIG. 9, the spatial straight line 82 results from the spatial intersection of the two planes defined by the conical surfaces 40, 40'. The intersection of the two triangular surfaces establishes the straight line 82, i.e. the preferred direction, unambiguously and precisely.

As explained above, the spatial straight line 82 can be used according to the invention intraoperatively to navigate the drill 14. This operation is described in greater detail below with reference to FIGS. 10 to 12.

First, how the spatial arrangement of the puncture point 74 can be visualized with respect to the spatial straight line 82 is, however, explained yet again with reference to FIGS. 8 and 9. For this purpose, the spatial intersection is determined of those conical surfaces that each correspond to the semicircular outline 78, 78' of the head 70 of the femur bone 12 in the images 50, 50'. As emerges from FIG. 9, the spatial intersection of the conical surfaces corresponding to the semicircular outlines 78, 78' is a visualized structure in the form of a spatial sphere 80. It should be pointed out that the position and shape of the sphere 80 can be created unambiguously and precisely using the semicircles (or the corresponding full circles) 78, 78'. An intersection of the sphere 80 with the spatial straight line 82 yields the spatial position of the puncture point 74.

An intraoperative visualization of the actual position of the drill 14 relative to the puncture point 74 therefore makes it possible to navigate the drill 14 in such a way that the drilling operation can be interrupted in good time before the puncture point 74 is reached. The visualization of the spatial straight line 82 also makes possible a safe navigation of the drill 14. In an intraoperative graphical representation of sphere 80, straight line 82 and drill 14, the distance between the tip of the drill 14 and the puncture point 74 is simultaneously indicated, for example, in numerical form. On going below a minimum distance, an additional audible warning signal is sounded.

Of course, the spatial straight line 82 and the sphere 80 in accordance with FIG. 9 can also be represented in the three-dimensional graphical representations in accordance with FIGS. 5 and 6 to facilitate the navigation of the surgical instrument 14.

Figure 10:
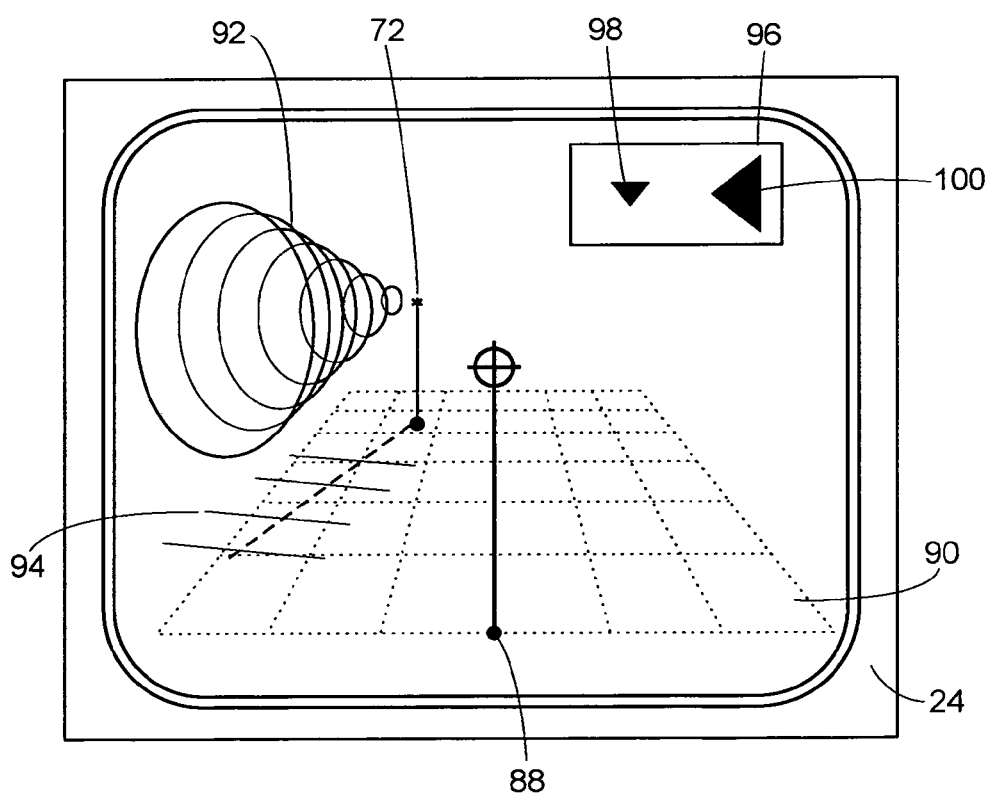
FIGS. 10 to 12 show a navigation aid according to the invention.
Figure 11:
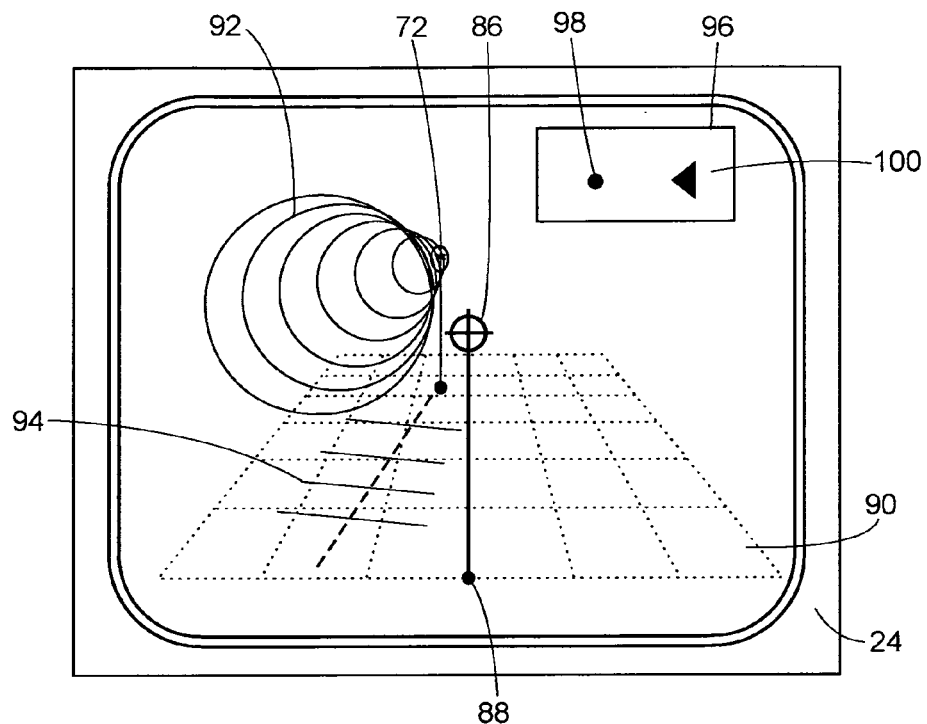
Figure 12:
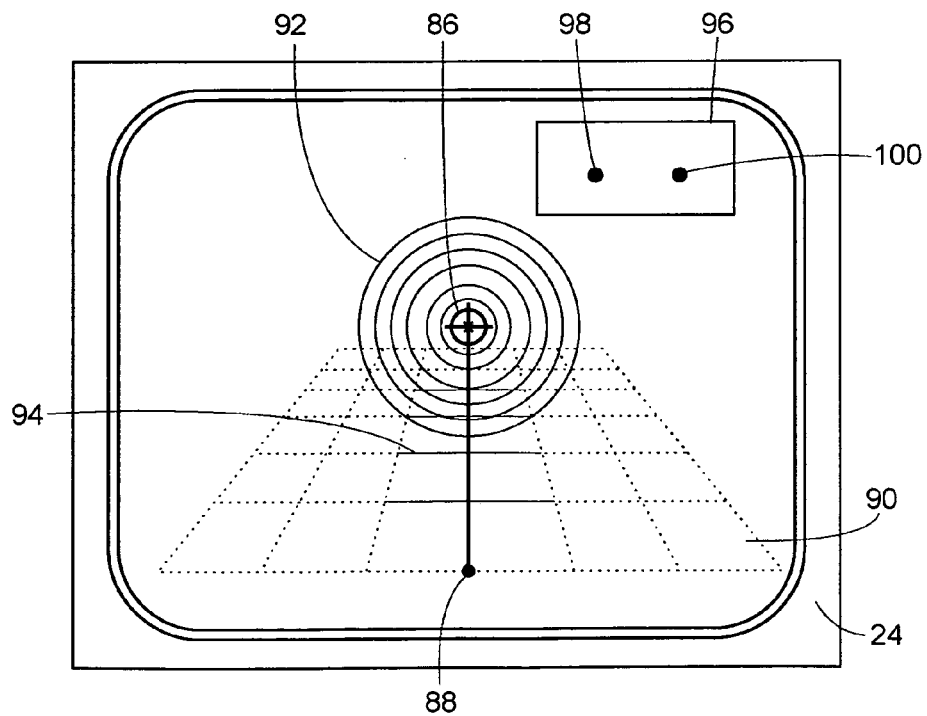

A graphical navigation aid according to the invention for a surgical instrument by way of example for the surgical intervention shown in FIGS. 7 to 9 is explained below with reference to FIGS. 10 to 12. To support the navigation of the drill 14 shown in FIG. 7 in such a way that it enters the head 70 of the femur bone 12 along the spatial straight line 82 shown in FIG. 9, a graphical navigation aid is shown on the viewing screen 24 shown in FIG. 1. Said navigation aid comprises crosshairs 86 that mark the tip of the drill 14 shown in FIG. 7. The point 88 denotes a projection of the tip of the drill 14 on a horizontal plane 90. The point 72 on the viewing screen 24 denotes the desired entry point of the drill 14 into the femur bone 12. The point 72 is visualized as shown in FIGS. 10 to 12 in the same way as described above with reference to FIGS. 7 to 9 for the straight line 82 and the sphere 80. A tunnel-type structure 92 serves as reference point for the relative position of the spatial straight line 82 relative to the effective axis of the drill 14. Said effective axis extends at a right angle from the position of the crosshairs 86 out of the plane of the drawing. A projection 94 of the geometrical straight line 82 can furthermore be seen on the horizontal plane 90.

At the top right of the viewing screen 24, a direction indicator 96 is shown. Said direction indicator 96 indicates the direction in which the tip of the drill 14 has to be moved in order to align the drill 14 along the geometrical straight line 82 symbolized by the tunnel 92. In the case shown in FIG. 10, the drill 14 has to be moved slightly downwards and relatively far to the left. This emerges from a small arrow pointing downwards in the representation field 98 and a large arrow pointing left in the representation field 100.

FIG. 11 shows the case where the drill 14, proceeding from the position shown in FIG. 10 has been moved slightly downwards and slightly to the left. As is indicated by the point in the representation field 98, the tip of the drill 14 symbolized by the crosshairs 86 is now situated in the same horizontal plane as the spatial straight line 82 corresponding to the tunnel structure 92. As is made clear, however, by the small arrow in the representation field 100 pointing to the left, the drill 14 must still be moved slightly to the left in order to align the effective axis of the drill 14 along the geometrical straight line 82 symbolized by the tunnel 92.

If the drill 14 is now moved slightly to the left, the viewing-screen content results that is shown in FIG. 12. In the direction indicator 96, two points are now shown. This diagram indicates that the effective axis of the drill 14 is aligned along the preferred direction indicated by the tunnel structure 92.

In this position, the surgeon can now switch the viewing screen to another representation mode in order to choose, for example, a three-dimensional visualization of a structure to be surgically treated corresponding to the viewing-screen printout in accordance with FIG. 6.

We claim:

1. Method for navigating in the interior of the body using three-dimensionally visualized structures, comprising the following steps:
    providing at least two two-dimensional images (50, 50') of the same anatomical object (12) from different perspectives and also of information which makes it possible to draw a conclusion about the respective spatial position of an imaging system (26) relative to the anatomical object (12);
    defining a projection (76, 76', 78, 78') of a geometrical structure (72, 80, 82) to be visualized or a part thereof in each two-dimensional image, wherein the geometrical structure (72, 80, 82) to be visualized is different from the anatomical object (12);
    generating a conical surface (40, 40') in space for every image (50, 50'), wherein the spatial positions of cone vertex (46, 46') and cone directrix are determined from the respective spatial position of the imaging system (26) and the shape of the cone directrix is determined from the shape of the projection (76, 76', 78, 78') of the geometrical structure (72, 80, 82) to be visualized;
    forming a spatial intersection of the individual conical surfaces (40, 40') to determine the geometrical structure (72, 80, 82); and
    displaying the geometrical structure (72, 80, 82) determined and/or an intersection (74) of a plurality of geometrical structures (72, 80, 82) determined and using the representation for navigation.

2. Method according to claim 1, characterized in that the created projection of the geometrical structure (72, 80, 82) is a point, a straight line (76, 76'), a circular segment (78, 78') or another structure having the form of a line.

3. Method according to claim 1 or 2, characterized in that the geometrical structure to be visualized is a point (72), a straight line (82), a plane, a sphere (80) or another two-dimensional or three-dimensional structure.

4. Method according to claim 1, 2 or 3, characterized in that the two-dimensional images (50, 50') are generated by X-ray methods and/or magnetoresonance methods.

5. Method according to one of claims 1 to 4, characterized in that the spatial intersection is revised using at least one further data set of the anatomical object (12).

6. Method according to claim 5, characterized in that a two-dimensional or three-dimensional image or a generic model of the anatomical object (12) is used as further data set.

7. Method according to one of claims 1 to 6, characterized in that suitable perspectives are determined for further two-dimensional images by inverse calculations.

8. Method according to one of claims 1 to 7, characterized in that, additionally, the spatial position of an instrument (14) to be navigated is shown graphically relative to the geometrical structure (72, 80, 82) or to the intersection (74).

9. Method according to one of claims 1 to 8, characterized in that the effective axis (60, 60', 60", 60''') of a surgical instrument (14) is shown graphically.

10. Method according to one of claims 1 to 9, characterized in that the individual two-dimensional images (50, 50', 50", 50''') are shown graphically taking account of the positions (46, 46') from which the images were taken.

11. Method according to one of claims 1 to 10, characterized in that a navigation aid in the form of a tunnel structure (92) is shown graphically.

12. Method according to claim 11, characterized in that, in addition to the navigation aid (92), a separate direction indicator (96) is shown graphically for the navigation of the surgical instrument (14).

13. Method for navigating in the interior of the body using three-dimensionally visualized structures, comprising the following steps:
    providing at least two two-dimensional X-ray images (50, 50') of the same bone (12) from different perspectives, of information that makes it possible to draw conclusions about the respective spatial position of an X-ray imaging system (26) relative to the bone (12), and also a magnetoresonance data set of the bone (12);
    defining a projection (76, 76', 78, 78') of a surface or of an outline of the spongiosa of the bone (12) in every two-dimensional X-ray image;
    generating a conical surface (40, 40') in space for every image (50, 50'), wherein the spatial positions of cone vertex (46, 46') and cone directrix are determined from the spatial position of the imaging system (26) and the shape of the cone directrix is determined from the shape of the defined projection;
    forming a spatial intersection of the individual cone surfaces (40, 40') to determine a first model of the spongiosa;
    determining a second model of the spongiosa from the magnetoresonance data set;
    generating a representation of the bone (12) by combining the two models and use of the representation for the purpose of navigation.

* * * * *